United States Patent [19]

Davidonis et al.

[11] Patent Number: 4,672,035

[45] Date of Patent: Jun. 9, 1987

[54] CONTROLLED REGENERATION OF COTTON PLANTS FROM TISSUE CULTURE

[75] Inventors: Gayle H. Davidonis; Ralph O. Mumma; Robert H. Hamilton, all of State College, Pa.

[73] Assignee: Research Corporation, New York, N.Y.

[21] Appl. No.: 590,112

[22] Filed: Mar. 16, 1984

[51] Int. Cl.$^4$ .................... C12N 5/00; C12N 5/02; A01B 79/00; A01C 1/00

[52] U.S. Cl. .................... 435/240; 435/241; 47/58

[58] Field of Search .................... 435/240, 241; 47/58

[56] References Cited

U.S. PATENT DOCUMENTS 4,038,778 8/1977 Kadkade .
4,204,366 5/1980 Janick et al. .
4,326,034 4/1982 Peel et al. .

OTHER PUBLICATIONS

Davidonis et al, 1983, "Plant Regeneration From Callus Tissue of *Gossypium Hirsutum L.*", *Plant Sci. Lett*, v 32, pp. 89–93.
Smith et al, 1977, "Defined Conditions for the Initiation and Growth of Cotton Callus . . . ", *In Vitro*, v 13, pp. 329–334.
Conger, (Editor), 1981, *Cloning Agricultural Plants Via In Vitro Techniques*, CRC Press, Boca Raton, p. 196.
Weier et al, 1970, Botany An Introduction to Plant Biology, 4th Ed, John Wiley & Sons, N.Y. p. 680.
Williams, 1978, "Conditions for Optimal Growth and Differentiation of *Gossypium hirsutum L.* Tissue Cultures" PhD Dissertation, pp. 24–107.

*Primary Examiner*—Thomas G. Wiseman
*Assistant Examiner*—David T. Fox
*Attorney, Agent, or Firm*—Scully, Scott, Murphy & Presser

[57] ABSTRACT

The regeneration of plants from cotton callus (*Gossypium hirsutum* L. cv Coker 310) is described. Somatic proembryoids developed spontaneously after two years in culture on a modified Linsmaier and Skoog medium. The percentage of calli forming proembryoids was increased to about 30% by prolonged culture without NAA and kinetin. Development of proembryoids was enhanced by transferring proembryoids to media lacking $NH_4NO_3$ but containing double the standard $KNO_3$ concentration and gibberellic acid. Root initiation and growth was promoted by lowering the glucose concentration to 5 g/l.

13 Claims, No Drawings

CONTROLLED REGENERATION OF COTTON PLANTS FROM TISSUE CULTURE

FIELD OF THE INVENTION

This invention relates to the area of plant cell morphogenesis. More specifically, this invention relates to a method for the controlled regeneration of cotton plants from tissue culture.

BACKGROUND OF THE INVENTION

Investigations concerning the morphogenesis of plant tissue in culture date back at least to the 1950's (Skoog, F. and Miller C. O. Symp Soc. Exp. Biol., 11:118 (1957)) and have continued apace to date. Several monographs provide extensive reviews of the field and contain compilations of numbers of species which will undergo plant regeneration in culture (See for example, Murashige T., In: "Propagation of Higher Plants through Tissue Culture," T. A. Thorpe, Ed., p. 15, Univ. Calgary Press, Calgary (1978); Vasil, I,K, et al Adv. Gent. 20:127 (1979) and Evans. D. A., et al In: "Plant Tissue Culture: Methods and Applications in Agriculture: T. A. Thorpe, Ed. pg. 45, Academic Press, New York (1981)).

The term "plant tissue culture" as used herein is taken in its broadest meaning to refer to the cultivation, in vitro, of all plants parts, whether a single cell, a tissue or an organ, under aseptic conditions. More restrictive terms relating to plant tissue culture technology include: "callus culture" by which is meant, the culture of cell masses on agar medium and produced from an explant of a seedling or other plant source; "cell culture" by which is meant, the culture of cells in liquid media in vessels which are usually aerated by agitation; "organ culture" by which is meant, the aseptic culture on nutrient media of embryos anthers (microospores), ovaries, roots, shoots, or other plant organs; "meristem culture and morphogenesis" by which is meant, the aseptic culture of shoot meristems or other explant tissue on nutrient media for the purpose of growing complete plants, and "protoplast culture" by which is meant, the aseptic isolation and culture of plant protoplasts from cultured cells or plant tissue.

On their face, the principles underlying plant tissue culture are quite simple. Initially, it is necessary to isolate a plant part from the intact plant and disrupt its organ, inter-tissue, and inter-cellular relationships. Subsequently, it is necessary to provide the isolated material with the appropriate environment in which to express its intrinsic or induced developmental potential. Finally, the steps must be carried out aseptically. Although the principles may be simply stated, as a matter of practice, the successful culture of plant tissue and its regeneration into a mature plant is extremely complex. The impressive list of plants species cited herein below, for which successful regeneration has been achieved, belies the difficulties in achieving those results. As will be noted later, successful regeneration of a particular species is often characterized by the addition of (or even omission of) catalytic amounts of auxins, cytokinins, or other growth regulators. Further, successful regeneration may also be a function of not only the mere presence of a certain compound but its ratio to other media components as well. Since each plant species appears to possess a relatively unique optimal set of media requirements, the successful preparation and regeneration of a new species cannot be necessarily inferred from the successful regimens applied to unrelated plant varities. This is not to say that broad generalizations as to procedure are not possible. For example, if the goal of the tissue culture system is vegetative propagation, then the regeneration may be envisioned to comprise three stages. The first stage occurs following the transfer of an explant onto a culture medium. This stage is characterized by a proliferation of the explant or callus. The second stage is characterized by a rapid increase in organ growth. This stage may require a transfer to a second medium with or without a change in growth regulator concentration. The final stage occurs when the plants are removed from in vitro culture and requires the establishment of the autotrophic state.

As mentioned previously, organogenesis or embryogenesis has been reported for a variety of species. Plant regeneration has been achieved from explants of cotyledon, hypocotyl, stems, leaf, shoot apex, root, young infloresences, flower petals, petioles, ovular tissue and embryos. For a particular species the source of the explant may be important for the success of the subsequent regeneration. The size and the shape of the explant may also be critical. Another element to be considered is the method of providing aseptic explant material for purpose of callus formation. This involves sterilization of the explant tissue prior to inoculation onto propagation medium. Even this apparently routine process is subject to a wide variety of critical experimental parameters. To illustrate this point Table I shows the extreme variability in experimental protocols for the sterilization procedures alone.

TABLE I

| Explant | Plant | Size | Sterilization protocol | Remarks |
| --- | --- | --- | --- | --- |
| Leaf blade | tomato | 6 × 8 mm | wash in detergent, 10 min. in 7% Clorox[a], wash twice in water | young leaves near shoot apex |
| Stem | rape | 5 mm | rinse in 70% ethanol, 6 min. in 10% Clorox, wash four times in water | basal end in contact with medium |
| Embryo | cacao | 2.5–25 mm intact | 15 min in 10% Clorox with 0.1% Tween 20 | use pods larger than 12 cm |
| Storage organ | artichoke | 2.4 × 2 mm | 30 min in 20% Clorox, wash repeatedly | use storage parenchyma region |
| Seed (root) | petunia | 3 mm | 30 min. 50% Clorox, wash three times in water | use 4–6 days after germination |
| Seed (hypocotyl) | flax | 4–8 mm | 1 min. in 70% ethanol, 20 min. in 20% Clorox, | use 5 days after germi- |

TABLE I-continued

| Explant | Plant | Size | Sterilization protocol | Remarks |
|---------|-------|------|------------------------|---------|
|         |       |      | wash in water          | nation  |

[a]Clorox ®, a commercial bleach, is a 5% solution of sodium hypochlorite.
After: Evans et al supra Once the explant is placed onto a suitable medium callus formation may occur. Only a small percentage of the cells from an explant will give rise to the callus. A variety of factors have been reported to effect callus proliferation; medium composition, size and shape of the original explant, friability of cells of the callus and even the season of the year. The latter factor likely a reflection of changes in endogenous levels of growth regulating substances.

Somatic embryogenesis can then proceed directly from either a population of sporophytic or gametophytic cells or alternatively from embryogenic cells obtained from epigenetic redetermination of callus cells. Regardless of the mode of embryogenesis, the manipulation of growth regulators are extremely important. This fact is illustrated in Table II.

TABLE II

| Crop | Species | Growth Regulators 1° Medium | Growth Regulators 2° Medium | Medium | Explant |
|------|---------|------------------------------|------------------------------|--------|---------|
| Anise | Pimpinella anism | 5 μM 2,4-D | none | B5 | hypocoytl |
| Asparagus | Asparagus officinalis | 5.4 μM NAA<br>4.7 μM KIN | 0.5–5.7 μM IAA<br>0.4–17.7 μM 6BA | LS or MS | cladodes shoots |
| Cacao | Theobroma cacoa[a] | none<br>10% CW | 6.4 μM NAA<br>10% CW | MS | imm. embryo cotyledon |
| Cauliflower | Brassica oleracea | 5.7 μM IAA<br>2.0 μM KIN | 5.7 μM IAA | MS | leaf |
| Caraway | Carum carvi | 10.7 μM NAA | none | MS | petiole |
| Carrot | Dacus carota | 4.5 μM 2,4-D | none | MS | storage root |
| Celery | Apium graveolens | 2.2 μM 2,4-D | 2.7 μM KIN | MS | petiole |
| Coffee | Coffea arabica | 18.4 μM KIN<br>4.5 μM 2,4-D | 2.3 μM KIN<br>0.27 μM NAA | MS | leaf |
| Coffee | Coffea canephora | 2 μM KIN | 2.5 μM KIN | MS | leaf |
| Coriander | Coriandrum sativum | 10.7 μM NAA | none | MS | embryo |
| Cotton | Gossypium klotzschianum | 0.5 μM 2,4-D | 11.4 μM IAA<br>4.7 μM KIN | MS | hypocotyl |
| Date Palm | Phoenix dactylifera | 452 μM 2,4-D<br>4.9 μM 2iP | none | MS | ovule |
| Dill | Anethum graveolens | 10.7 μM NAA<br>2.3 μM 2,4-D<br>2.3 μM KIN | none<br>none | MS<br>White | embryo<br>inflorescence |
| Eggplant | Solanum melongena | 5 μM NOA | 4.7 μM KIN | MS | hypocotyl |
| Fennel | Foeniculum vulgare | 27.6 μM 2,4-D<br>1 μM KIN | none | Nitsch | stem |
| Garlic | Allium sativa | 10 μM CPA<br>2 μM.2,4-D<br>0.5 μM KIN | 10 μM IAA<br>20 μM KIN | AZ | stem |
| Ginseng | Panax ginseng | 2.2 μM 2,4-D<br>0.8 μM KIN | 0.4 μM 2,4-D | MS | pith |
| Grapes | Vitis spp. | 4.5 μM 2,4-D<br>0.4 μM 6BA | 10.7 μM NAA<br>0.4 μM 6BA | MS | flower, leaf |
| Oil Palm | Elaeis guineensis | 4.5 μM 2,4-D<br>2.3 μM KIN | 5.7 μM IAA | Heller | embryo |
| Orange | Citrus sinensis | 0.5 μM KIN<br>5.7 μM IAA | none | Murashige, Tucker | ovule |
| Parsley | Petroselinum hortense | 27 μM 2,4-D | none | Hildebrandt C | petiole |
| Pumpkin | Cucurbita pepo | 4.9 μM IBA | 1.4 μM 2,4-D | MS | cotyledon hypocotyl |
| Sandalwood | Santalum album | 9.1 μM 2,4-D<br>23.2 μM KIN | none | White | embryo |
|  | S. album | 4.5 μM 2,4-D<br>0.9–2.3 μM KIN | 1.5–5.8 μM GA$_3$ | MS<br>White | stem |
| Sweet Gum | Liquidambar styraciflua | 5.3 μM NAA<br>8.8 μM 6BA | none | Blaydes | hypocotyl |
| Water Parsnip | Sium suave | 10.7 μM NAA | none | MS | embryo |
| Papaya | Carica papaya | 1 μM NAA | 0.1 μM NASA | White | petiole |

TABLE II-continued

| Crop | Species | Growth Regulators | | Medium | Explant |
|------|---------|-------------------|-------------|--------|---------|
|      |         | 1° Medium         | 2° Medium   |        |         |
|      |         | 10 μM 2iP         | 0.01 μM 6BA |        |         |

<sup>a</sup>Requires a subculture on a maintenance medium prior to 2° culture.
After: Evans et al supra
Abbreviations
auxins:
IAA = indole acetic acid;
IBA = indole butyric acid;
2,4-D = 2,4-dichlorophenoxyacetic acid;
NAA = naphthaleneacetic acid;
pCPA = para-chlorophenoxyacetic acid;
NOA = B-napthoxyacetic acid;
BTOA = 2-benzothiazole acetic acid;
PIC = picloram;
2,4,5-T = 2,4,5-tichlorophenoxyacetic acid;
cytokinins:
KIN = kinetin;
6BA = 6 benzyladenine (benzylaminopurine)
2iP = 2 isopentenyl adenine;
ZEA = zeatin;
other growth regulators:
ADE = adenine;
CW = coconut water;
CH = casein hydrolysate;
ABA = abscisic acid;
$GA_3$ = gibberellic acid.
Medium
MS = Murashige and Skoog
B5 = Gamborg
SH = Schenk and Hildebrandt
W = White
LS = Linsmaier and Skoog Even though cotton is listed among those species for which embryogenesis had occurred, the development of the embryoids into plants was not achieved. The cotton species used in those experiments was not a cultivated cotton of commercial value but a lintless wild cotton.

It is the object of this invention to provide a method for the controlled regeneration of cotton plants from tissue culture.

BRIEF DESCRIPTION OF THE INVENTION

This invention relates to methods for the controlled regeneration of cotton plants from tissue culture. The invention is characterized by providing a method for the controlled regeneration of a cotton plant from callus culture comprising:
providing a callus;
transferring said callus to a first, regeneration conditioning medium;
culturing said callus for a sufficient period of time to promote the formation of proembryoids;
transferring said proembryoids to a second, regeneration promoting medium; and
culturing said proembryoids for a sufficient period of time to promote the development of said proembryoids into plantlets.

DETAILED DESCRIPTION OF THE INVENTION

This invention provides methods for the controlled regeneration of cotton plants from tissue culture. The successful recovery of plantlets was predicated upon the discovery that three culture parameters are critically important. These parameters are: (1) The condition of the callus prior to initiation of regeneration, (2) The stepwise regeneration protocol; and (3) the source and amount of assimilable nitrogen.

Callus Formation

Callus useful in the subject invention was generated according to the following procedure:

Cotton callus tissue was derived from cotyledons of *G. hirsutum* cv Coker 310. After delinting, the seeds were surface sterilized for 10 minutes in a 50% solution of commercial bleach, (2.6% sodium hypochlorite) and rinsed with sterile distilled water. The seeds were germinated in sterile petri dishes containing filter paper moistened with distilled water. Tissue pieces were excised from expanding cotyledons and transferred to a Linsmaier and Skoog (LS) medium) (Linsmaier, E. M. and Skoog, F, Physiol Plant. 18:100 (1965)) containing 8.5 g/l agar, 30 g/l glucose, 2 mg/l α-naphthanlene acetic acid (NAA) and 1 mg/l kinetin. After 3 months cotyledon tissue gave rise to friable slow growing gray calli. The callus tissue was subcultured on a modified Linsmaier and Skoog's agar media containing 30 g/l glucose, 1 mg/l NAA and, 0.5 mg/l kinetin. Cultures were maintained under continuous low light conditions (0.5 to 1.0 $E/m^2.s$) at 25° C. The slow growing callus tissue was subcultured every 6 or 7 weeks. Over a three year period, three callus lines were derived: line 1 was a granular light beige callus, line 2 was a fast growing green habituated callus and line 3 was a gray soft callus. Although all callus lines formed a few proembryoids, roots were regularly formed only on lines 2 and 3. The most preferred callus for use is the gray, soft callus.

TABLE III

Composition of Media Use in Controlled Regeneration of Cotton Plants

| Ingredient | Linsmaier and Skoog (1965) LS mg/L | modified LS mg/L | modified LS, 2xKNO₃ mg/L | modified LS, 2xKNO₃ + .1 mg/L GA mg/L | modified 2xKNO₃—NAA,-K mg/L |
|---|---|---|---|---|---|
| $NH_4NO_3$ | 1650 | 1650 | 0 | 0 | 0 |
| $KNO_3$ | 1900 | 1900 | 3800 | 3800 | 3800 |
| $CaCl_2.2H_2O$ | 440 | 440 | 440 | 440 | 440 |
| $MgSO_4.7H_2O$ | 370 | 370 | 370 | 370 | 370 |
| $KH_2PO_4$ | 170 | 170 | 170 | 170 | 170 |
| $FeSO_4.7H_2O$ | 27.8 | 27.8 | 27.8 | 27.8 | 27.8 |
| $Na_2.EDTA.2H_2O$ | 37.3 | 37.3 | 37.3 | 37.3 | 37.3 |
| $H_3BO_3$ | 6.2 | 6.2 | 6.2 | 6.2 | 6.2 |
| $MnSO_4.4H_2O$ | 22.3 | 22.3 | 22.3 | 22.3 | 22.3 |
| $ZnSO_4.7H_2O$ | 8.6 | 8.6 | 8.6 | 8.6 | 8.6 |
| KI | 0.83 | 0.83 | 0.83 | 0.83 | 0.83 |
| $Na_2MoO_4.2H_2O$ | 0.25 | 0.25 | 0.25 | 0.25 | 0.25 |
| $CoCl_2.6H_2O$ | .025 | .025 | .025 | .025 | .025 |
| $CuSO_4.5H_2O$ | .025 | .025 | .025 | .025 | .025 |
| inositol | 100 | 100 | 100 | 100 | 100 |
| thiamine.HCl | 0.4 | 0.4 | 0.4 | 0.4 | 0.4 |
| sucrose | 30,000 | 0 | 0 | 0 | 0 |
| glucose | 0 | 30,000 | 30,000 | 30,000 | 30,000 |
| IAA | 1–30 | 0 | 0 | 0 | 0 |
| NAA | 0 | 1 | 1 | 1 | 0 |
| kinetin | .001–10 | .5 | .5 | .5 | 0 |
| gibberellic acid | 0 | 0 | 0 | .1 | 0 |
| agar | 10,000 | 8,500–9,000 | 8,500–9,000 | 8,500–9,000 | 8,500–9,000 |

Alterations in media composition included adjustments inorganic salt concentrations, elimination of NAA and kinetin, addition of gibberellic acid ($GA_3$) or changes in the glucose concentration. Some proembryoid cultures and plants were grown under continuous light conditions at a higher light intensity (58 $E/m^2.s$). The details of the various media compositions used herein are shown in Table III.

One month after transfer to a first conditioning medium callus tissue was scored visually for the appearance of proembryoids. Proembryoids were defined as yellow or green globular structures (1 mm in diameter) produced on the surface of an otherwise gray-green callus. Proembryoids were transferred to a second new regeneration promoting medium, and their development was monitored over a one-month period.

It was suprisingly discovered that callus maintained in culture for periods of one to two years or more were competent to yield plants upon regeneration according to the subject invention. It is not necessarily required to culture the callus for such extended periods of time in order to achieve proembryoid formulation. As detailed hereinbelow proembryoid formulation can be achieved 6–10 months after callus initiation.

Stepwise Regeneration

Six month-three year old cotton callus tissue was cultured for 13 weeks on a first regeneration conditioning medium comprising LS medium and 30 g/l glucose. The medium did not contain NAA or kinetin.

By selection techniques (selection of embyrogenic callus) thirty to fifty percent of the callus pieces developed proembryoids in 4 weeks. Callus tissue (about 135 mg pieces) will grow on media lacking NAA and kinetin for at least two transfers. The increased embryogenic potential of callus tissue after 13 weeks without hormones can be maintained for at least three transfers on media containing NAA and kinetin. Callus tissue was normally transferred every 6 or 7 weeks but if the interval between transfers was greater than 15 weeks, subsequent callus growth and embryogenic potential were greatly reduced. The callus was then transferred to a second regeneration promoting medium comprising either or modified LS medium without NAA or kinetin or a modified LS medium with NAA and kinetin.

Proembryoid development proceded in several directions and in many cases stopped before leaf production. Proembryoids increased in size and developed into cylindrical embryoids or took on a coiled form. Gibberellic acid (0.1 mg/l) enhanced elongation of embryoids. In cylindrical embryoids and coiled embryoids, one pole grew out to produce "leaves" (abnormal leaf-like structures) with vascular tissue or "leaves" with vascular tissue, stomates and pigment glands. Some embryoids in which only vascular tissue had differentiated later developed into dark green calli. It appeared that as soon as stomates were formed pigment glands would differentiate. Adventitious roots were formed before or after "leaf" development. More normal leaves appeared after the development of the initial leaf-like structures. After 4 normal appearing leaves were formed, plants were subjected to a "potting-up" procedure comprising transferring the plants to vermiculite (2½ inch pots) and watering weekly with one-fourth strength LS salts. Then 4 to 6 weeks later, plants were transferred to soil and moved to a greenhouse. Plants grown in the greenhouse appeared normal and several have flowered, produced normal cotton bolls and viable seeds. The regeneration process from proembryoid development to plant was accomplished in three or more months depending on the number of initial leaf-like structures produced before normal leaf development.

When proembryoids were transferred to LS media lacking $NH_4 NO_3$ and containing double the $KNO_3$ concentration, more of the proembryoids developed into leaf-stem type structures. This degree of development occurred in media containing no hormone or NAA, kinetin and 0.1 mg/l $GA_3$ (Table IV). Embryoid growth was slower in media lacking hormones. Transferring advanced leaf-stem embryoids to media containing 5 g/l glucose enhanced root formation. Of the embryoids that reached the leaf-stem stage about 50% of these continued growing and produced normal looking plants.

A normal requisite for somatic embryogenesis in some plants is a reduced nitrogen supply. Cotton callus described herein readily formed globular proembryoids without a major adjustment in the reduced nitrogen supply. However, removal of ammonium nitrogen in conjunction with the addition of $GA_3$ seemed to favor proembryoid development to more advanced stages. Other favorable treatments included omission of NAA and kinetin, and reduction in the glucose to 5 g/l to promote root formation.

In a further embodiment proembryoids were obtained from an alternative source of tissue, hypoeotyl, from Coker 310 in a total of ten months and the details are as follows.

Callus tissue was initiated from Coker 310 hypocotyl explants. The original explant was placed on modified LS and then to encourage further proliferation transferred to modified LS with elevated hormone levels (5 mg/L NAA, 1 mg/L kinetin). After soft gray callus was formed, the callus was subcultured on modified LS with 2 mb/L NAA and 1 mg/L kinetin. Callus tissue was then transferred to modified LS medium lacking NAA and kinetin for 14 weeks. Proembryoids were formed when this callus was transferred to modified LS medium lacking NAA and kinetin or modified LS medium with 1 mg/L NAA and 0.5 mg/L kinetin.

In yet another embodiment, proembryoids were obtained from an alternative cotton variety, Coker 312, in a total of six months and the details are as follows.

Callus tissue was initiated from Coker 312 hypocotyl explants. Callus was initiated on modified LS medium with 2 mg/L NAA and 1 mg/L kinetin and then transferred for 16 weeks to medium lacking NAA and kinetin. Proembryoids were formed when callus was transferred to modified LS medium.

modified by substituting 30 g/L glucose for sucrose;

culturing said callus for a sufficient period of time to promote the formation of proembryoids;

transferring said proembryoids to a second, regeneration promoting modified LS medium, which has been modified by substituting glucose for sucrose; and culturing said proembryoids for a sufficient period of time to promote the development of said proembryoids into plantlets.

2. The method according to claim 1 including the further step of recovering said plantlets and potting-up same to provide a cotton plant.

3. The method according to claim 1 therein said cotton plant is *Gossypium hirsutum* L.

4. The method according to claim 3 wherein said cotton plant is *Gossypium hirsutum* L. cv Coker 310.

5. The method according to claim 3 wherein said cotton plant is *Gossypium hirsutum* L. cv Coker 312.

6. The method according to claim 1 wherein said callus is derived from a source selected from the group consisting of cotyledon, hypocotyl, stem, leaf, shoot apex, root, young inflorescences, flower petals, petioles ovular tissue and embryos.

7. The method according to claim 6 wherein said callus is derived from cotyledon.

8. The method according to claim 6 wherein said callus is derived from hypocotyl.

9. The method according to claim 1 wherein said proembryoid forming step is carried out from about 5 to about 15 weeks.

10. The method according to claim 9 wherein said step is carried out for about 13 weeks.

11. The method according to claim 1 wherein said second medium comprises an NAA and kinetin-free modified LS medium, which has been further modified

TABLE IV

| | THE PERCENTAGE PROEMBRYOIDS REACHING THE LEAF-STEM STAGE AFTER TRANSFER TO A SECOND REGENERATION PROMOTING MEDIUM | | | |
|---|---|---|---|---|
| | SECOND MEDIUM | | | |
| | Modified LS | Modified LS $-NH_4NO_3 + 2xKNO_3$ | Modified LS $-NH_4NO_3 + 2xKNO_3 +$ 0.1 mg/l $GA_3$ | Modified LS $-NH_4NO_3 +$ $2xKNO_3 - NAA -$ Kinetin |
| Percent of proembryoids at the leaf-stem stage[a] | 6 | 7 | 19 | 12 |

[a]Percentages are based on 65, 57, 57, and 52 proembryoids, respectively.

What is claimed is:

1. A method for the controlled regeneration of a cotton plant from callus culture comprising:

providing a callus;

transferring said callus to a first, regeneration conditioning medium comprising an NAA and kinetin-free modified LS medium, which has been further by substituting 5 g/L glucose for sucrose and $2 \times KNO_3$ for $NH_4NO_3$ and further modified by adding 0.1 mg/L gibberellic acid.

12. The method according to claim 1 wherein said plantlet regeneration step is carried out from about 2 to about 8 weeks.

13. The method according to claim 11 wherein said step is carried out for about 4 weeks.

* * * * *